(12) United States Patent
Dorn

(10) Patent No.: US 9,687,370 B2
(45) Date of Patent: *Jun. 27, 2017

(54) METHOD OF LOADING A STENT INTO A SHEATH

(75) Inventor: Jürgen Dorn, Neulussheim (DE)

(73) Assignee: C.R. Bard, Inc., Murray Hill, NJ (US)

(*) Notice: Subject to any disclaimer, the term of this patent is extended or adjusted under 35 U.S.C. 154(b) by 854 days.

This patent is subject to a terminal disclaimer.

(21) Appl. No.: 12/991,112

(22) PCT Filed: May 8, 2009

(86) PCT No.: PCT/EP2009/055592
§ 371 (c)(1),
(2), (4) Date: Nov. 4, 2010

(87) PCT Pub. No.: WO2009/135934
PCT Pub. Date: Nov. 12, 2009

(65) Prior Publication Data
US 2011/0060397 A1 Mar. 10, 2011

Related U.S. Application Data

(60) Provisional application No. 61/090,772, filed on Aug. 21, 2008.

(30) Foreign Application Priority Data

May 9, 2008 (GB) .................................. 0808454.3
Aug. 21, 2008 (GB) .................................. 0815339.7

(51) Int. Cl.
*A61F 2/06* (2013.01)
*A61F 2/95* (2013.01)
*A61F 2/97* (2013.01)

(52) U.S. Cl.
CPC .................. *A61F 2/95* (2013.01); *A61F 2/97* (2013.01); *A61F 2002/9522* (2013.01)

(58) Field of Classification Search
CPC .... A61F 2/95; A61F 2002/9522; A61F 2/958; A61F 2002/9583; A61F 2/962; A61F 2/966; A61F 2002/9665; A61F 2/97
(Continued)

(56) References Cited

U.S. PATENT DOCUMENTS 3,953,566 A * 4/1976 Gore .............................. 264/505
3,962,153 A * 6/1976 Gore .............................. 521/79
(Continued)

FOREIGN PATENT DOCUMENTS

DE 10339628 A1 * 3/2005 ............... A61F 2/82
EP 0732087 A1 9/1996
(Continued)

OTHER PUBLICATIONS

Translation of DE10339628.*
(Continued)

*Primary Examiner* — Melanie Tyson
*Assistant Examiner* — Erin Collelo
(74) *Attorney, Agent, or Firm* — C.R. Bard Intellectual Property

(57) ABSTRACT

There is disclosed herein a method of loading a self-expanding stent (10) into a delivery sheath (12) that is by itself strong enough to preserve the stent in a radially compressed pre-deployment configuration, comprising the steps of: (i) compressing the stent (10) to a relatively small diameter; (ii) providing a loading sheath (18) with an inner diameter d1; (iii) with the stent (10) exhibiting an outside diameter of d2, where d2<d1, providing relative translational movement between the stent (10) and the loading sheath (18), whereby the stent is accommodated within the lumen of the loading sheath (18); (iv) advancing the loading sheath (18), containing the stent (10), into the lumen (16) of the delivery sheath (12); and {v} deploying the stent into the
(Continued)

lumen (16) of the delivery sheath (12), by withdrawing the loading sheath (18) while restraining the stent (10) from axial movement out of the lumen (16) of the delivery sheath (12).

20 Claims, 7 Drawing Sheets

(58) Field of Classification Search
USPC ...... 623/1.11, 1.12, 1.2, 1.23; 264/479, 539, 264/540, 197, 198, 288.4, 208, 209.5, 264/210.1, 210.7, 291, 181
See application file for complete search history.

(56) References Cited

U.S. PATENT DOCUMENTS

| | | | |
|---|---|---|---|
| 4,187,390 A * | 2/1980 | Gore | 174/102 R |
| 4,636,162 A * | 1/1987 | Pavy et al. | 425/290 |
| 4,732,152 A | 3/1988 | Wallsten et al. | |
| 5,026,377 A * | 6/1991 | Burton | A61F 2/82 |
| | | | 606/108 |
| 5,087,394 A * | 2/1992 | Keith | 264/470 |
| 5,217,482 A | 6/1993 | Keith | |
| 5,324,261 A * | 6/1994 | Amundson et al. | 604/103.02 |
| 5,415,664 A * | 5/1995 | Pinchuk | A61F 2/95 |
| | | | 604/523 |
| 5,453,090 A | 9/1995 | Martinez et al. | |
| 5,626,605 A * | 5/1997 | Irie et al. | 623/1.1 |
| 5,647,857 A * | 7/1997 | Anderson et al. | 604/264 |
| 5,662,703 A | 9/1997 | Yurek et al. | |
| 5,690,644 A | 11/1997 | Yurek et al. | |
| 5,709,703 A | 1/1998 | Lukic et al. | |
| 5,718,861 A * | 2/1998 | Andrews et al. | 264/235 |
| 5,755,769 A | 5/1998 | Richard et al. | |
| 5,765,682 A * | 6/1998 | Bley et al. | 206/363 |
| 5,823,995 A | 10/1998 | Fitzmaurice et al. | |
| 5,824,041 A | 10/1998 | Lenker et al. | |
| 5,833,694 A | 11/1998 | Poncet | |
| 5,843,027 A | 12/1998 | Stone et al. | |
| 5,968,069 A | 10/1999 | Dusbabek et al. | |
| 5,992,000 A * | 11/1999 | Humphrey et al. | 29/516 |
| 6,027,510 A | 2/2000 | Alt | |
| 6,033,413 A * | 3/2000 | Mikus | A61F 2/0009 |
| | | | 604/102.01 |
| 6,063,092 A | 5/2000 | Shin | |
| 6,126,685 A | 10/2000 | Lenker et al. | |
| 6,149,681 A | 11/2000 | Houser et al. | |
| 6,162,244 A * | 12/2000 | Braun | A61F 2/82 |
| | | | 623/1.12 |
| 6,168,748 B1 * | 1/2001 | Wang et al. | 264/520 |
| 6,224,803 B1 * | 5/2001 | Tiernan | 264/166 |
| 6,254,628 B1 | 7/2001 | Wallace et al. | |
| 6,309,383 B1 * | 10/2001 | Campbell et al. | 606/1 |
| 6,425,898 B1 | 7/2002 | Wilson et al. | |
| 6,447,540 B1 * | 9/2002 | Fontaine et al. | 623/1.12 |
| 6,613,067 B1 * | 9/2003 | Johnson | 606/194 |
| 6,613,075 B1 | 9/2003 | Healy et al. | |
| 6,629,992 B2 * | 10/2003 | Bigus et al. | 623/1.12 |
| 6,645,238 B2 | 11/2003 | Smith | |
| 6,702,843 B1 * | 3/2004 | Brown et al. | 623/1.11 |
| 6,805,703 B2 * | 10/2004 | McMorrow | 623/1.11 |
| 6,830,575 B2 * | 12/2004 | Stenzel | A61F 2/95 |
| | | | 606/108 |
| 6,833,002 B2 * | 12/2004 | Stack et al. | 623/1.11 |
| 6,841,029 B2 | 1/2005 | Lim | |
| 6,902,575 B2 * | 6/2005 | Laakso | A61F 2/95 |
| | | | 623/1.11 |
| 6,946,092 B1 * | 9/2005 | Bertolino et al. | 264/512 |
| 7,309,349 B2 * | 12/2007 | Jackson | A61F 2/95 |
| | | | 623/1.11 |
| 7,785,360 B2 * | 8/2010 | Freitag | A61F 2/95 |
| | | | 606/108 |
| 7,815,669 B2 | 10/2010 | Matsuoka et al. | |
| 7,993,350 B2 * | 8/2011 | Ventura | A61B 17/3439 |
| | | | 606/108 |
| 8,308,789 B2 * | 11/2012 | Armstrong | A61B 17/12022 |
| | | | 623/1.11 |
| 8,359,721 B2 * | 1/2013 | Melsheimer | A61F 2/95 |
| | | | 29/235 |
| 8,414,528 B2 * | 4/2013 | Liu | A61F 2/0095 |
| | | | 604/103.05 |
| 8,535,368 B2 * | 9/2013 | Headley, Jr. | A61F 2/95 |
| | | | 623/1.12 |
| 8,568,467 B2 | 10/2013 | Dorn et al. | |
| 8,597,366 B2 * | 12/2013 | Shank | A61F 2/90 |
| | | | 623/23.68 |
| 8,852,257 B2 * | 10/2014 | Liu | A61F 2/958 |
| | | | 623/1.11 |
| 9,119,741 B2 * | 9/2015 | Liu | A61F 2/0095 |
| 9,125,761 B2 * | 9/2015 | Wood | A61F 2/95 |
| 2001/0001128 A1 * | 5/2001 | Holman | A61F 2/0095 |
| | | | 623/1.11 |
| 2001/0011180 A1 | 8/2001 | Fitzmaurice et al. | |
| 2001/0027323 A1 | 10/2001 | Sullivan et al. | |
| 2002/0055767 A1 * | 5/2002 | Forde | A61B 17/0057 |
| | | | 623/1.11 |
| 2002/0099431 A1 * | 7/2002 | Armstrong et al. | 623/1.11 |
| 2002/0180107 A1 * | 12/2002 | Jackson et al. | 264/288.4 |
| 2003/0083730 A1 * | 5/2003 | Stinson | A61F 2/95 |
| | | | 623/1.11 |
| 2003/0109886 A1 | 6/2003 | Keegan et al. | |
| 2003/0114912 A1 | 6/2003 | Sequin et al. | |
| 2003/0125709 A1 | 7/2003 | Eidenschink | |
| 2003/0139801 A1 | 7/2003 | Sirhan et al. | |
| 2003/0163193 A1 | 8/2003 | Widenhouse | |
| 2003/0204235 A1 * | 10/2003 | Edens et al. | 623/1.5 |
| 2004/0143272 A1 * | 7/2004 | Cully et al. | 606/108 |
| 2004/0143315 A1 * | 7/2004 | Bruun | A61F 2/95 |
| | | | 623/1.11 |
| 2004/0148007 A1 * | 7/2004 | Jackson et al. | 623/1.12 |
| 2004/0167603 A1 * | 8/2004 | Jackson | A61F 2/91 |
| | | | 623/1.12 |
| 2004/0199239 A1 * | 10/2004 | Austin et al. | 623/1.11 |
| 2004/0267346 A1 | 12/2004 | Shelso | |
| 2005/0004555 A1 | 1/2005 | Pursley | |
| 2005/0049667 A1 | 3/2005 | Arbefeuille et al. | |
| 2005/0113902 A1 | 5/2005 | Geiser et al. | |
| 2005/0240254 A1 | 10/2005 | Austin | |
| 2006/0015171 A1 * | 1/2006 | Armstrong | A61B 17/12022 |
| | | | 623/1.12 |
| 2006/0030923 A1 | 2/2006 | Gunderson | |
| 2006/0089627 A1 | 4/2006 | Burnett et al. | |
| 2006/0142838 A1 * | 6/2006 | Molaei et al. | 623/1.12 |
| 2006/0212105 A1 | 9/2006 | Dorn et al. | |
| 2006/0247661 A1 | 11/2006 | Richards et al. | |
| 2006/0259124 A1 | 11/2006 | Matsuoka et al. | |
| 2007/0050017 A1 | 3/2007 | Sims et al. | |
| 2007/0074805 A1 | 4/2007 | Leeflang et al. | |
| 2007/0270932 A1 * | 11/2007 | Headley | A61F 2/95 |
| | | | 623/1.11 |
| 2008/0118546 A1 | 5/2008 | Thatcher et al. | |
| 2008/0243224 A1 | 10/2008 | Wallace et al. | |
| 2009/0254169 A1 | 10/2009 | Spenser et al. | |
| 2009/0312828 A1 | 12/2009 | Vrba | |
| 2010/0049297 A1 | 2/2010 | Dorn | |
| 2010/0168835 A1 | 7/2010 | Dorn | |
| 2010/0249907 A1 | 9/2010 | Dorn et al. | |
| 2011/0137396 A1 | 6/2011 | Dorn et al. | |
| 2011/0137400 A1 | 6/2011 | Dorn et al. | |
| 2011/0137401 A1 | 6/2011 | Dorn et al. | |
| 2011/0137402 A1 | 6/2011 | Dorn et al. | |
| 2011/0184509 A1 * | 7/2011 | Von Oepen | A61F 2/95 |
| | | | 623/1.23 |
| 2012/0059448 A1 | 3/2012 | Parker et al. | |
| 2012/0143303 A1 | 6/2012 | Dorn et al. | |
| 2012/0302955 A1 * | 11/2012 | Liu | A61F 2/0095 |
| | | | 604/103.05 |
| 2012/0324696 A1 * | 12/2012 | Liu | A61F 2/958 |
| | | | 29/428 |
| 2013/0218256 A1 * | 8/2013 | Liu | A61F 2/0095 |
| | | | 623/1.12 |

(56) References Cited

U.S. PATENT DOCUMENTS

| | | | | |
|---|---|---|---|---|
| 2014/0379064 | A1* | 12/2014 | Pacetti | A61L 31/048 623/1.11 |
| 2014/0379065 | A1* | 12/2014 | Johnson | A61F 2/958 623/1.11 |
| 2015/0088241 | A1* | 3/2015 | Liu | A61F 2/958 623/1.11 |

FOREIGN PATENT DOCUMENTS

| | | | |
|---|---|---|---|
| EP | 0941713 | A1 | 9/1999 |
| EP | 1062966 | A1 | 12/2000 |
| EP | 0732087 | B1 | 6/2003 |
| EP | 1679095 | A1 * | 7/2006 |
| FR | 2688688 | A1 | 9/1993 |
| JP | S59-51863 | A | 3/1984 |
| JP | H09-512194 | A | 12/1997 |
| JP | 2000-116788 | A | 4/2000 |
| JP | 2001-9037 | | 1/2001 |
| JP | 2001-299926 | A | 10/2001 |
| JP | 2006-515786 | A | 6/2006 |
| WO | 8603398 | A1 | 6/1986 |
| WO | 9317636 | A1 | 9/1993 |
| WO | 9415549 | A1 | 7/1994 |
| WO | 9530385 | A1 | 11/1995 |
| WO | 9632078 | A1 | 10/1996 |
| WO | 9820812 | A1 | 5/1998 |
| WO | 0018329 | A1 | 4/2000 |
| WO | 0108599 | A1 | 2/2001 |
| WO | 02/38084 | A2 | 5/2002 |
| WO | 03002019 | A2 | 1/2003 |
| WO | 03002034 | A2 | 1/2003 |
| WO | 2004062458 | A2 | 7/2004 |
| WO | 2004066809 | A2 | 8/2004 |
| WO | 2004096091 | A1 | 11/2004 |
| WO | 2005072650 | A1 | 8/2005 |
| WO | 2006019626 | A2 | 2/2006 |
| WO | 2006020028 | A1 | 2/2006 |
| WO | 2006071245 | A1 | 7/2006 |
| WO | WO 2006071245 | A1 * | 7/2006 |
| WO | 2006086709 | A1 | 8/2006 |
| WO | 2006096229 | A1 | 9/2006 |
| WO | 2006130326 | A2 | 12/2006 |
| WO | 2007103666 | A2 | 9/2007 |
| WO | 2009050265 | A1 | 4/2009 |
| WO | 2010076052 | A1 | 7/2010 |
| WO | 2010076057 | A1 | 7/2010 |
| WO | 2010115925 | A1 | 10/2010 |
| WO | 2011067277 | A1 | 6/2011 |
| WO | 2011067280 | A1 | 6/2011 |
| WO | 2012072729 | A1 | 6/2012 |

OTHER PUBLICATIONS

Translation of EP0941713.*
English Translation of DE10339628.*
GB App. No. 0815339.7 filed Aug. 21, 2008 Search Report dated Dec. 22, 2008.
PCT/EP2009/055592 filed May 8, 2009 Search Report dated Aug. 3, 2009.
PCT/EP2009/060827 filed Aug. 21, 2009 Preliminary Report on Patentability dated Oct. 19, 2010.
PCT/EP2009/060827 filed Aug. 21, 2009 Search Report dated Nov. 16, 2009.
PCT/EP2009/060827 filed Aug. 21, 2009 Written Opinion dated Nov. 16, 2009.
PCT/EP2009/055592 filed May 8, 2009 Written Opinion dated Aug. 3, 2009.
PCT/EP2009/055592 filed May 8, 2009 International Preliminary Report on Patentability dated Nov. 9, 2010.
EP 12164925.5 filed Jul. 6, 2011 Extended European Search Report dated Jul. 26, 2012.
PCT/EP2009/064057 filed Oct. 26, 2009 International Preliminary Report on Patentability dated Jun. 6, 2011.
PCT/EP2009/064057 filed Oct. 26, 2009 International Search Report dated May 17, 2010.
PCT/EP2009/064057 filed Oct. 26, 2009 Written Opinion dated May 17, 2010.
PCT/EP2010/068620 filed Dec. 1, 2010 International Preliminary Report on Patentability dated Aug. 5, 2011.
PCT/EP2010/068620 filed Dec. 1, 2010 International Search Report dated Apr. 21, 2011.
PCT/EP2010/068620 filed Dec. 1, 2010 Written Opinion dated Apr. 21, 2011.
PCT/EP2010/068627 filed Dec. 1, 2010 International Preliminary Report on Patentability dated Jul. 20, 2011.
PCT/EP2010/068627 filed Dec. 1, 2010 International Search Report dated Apr. 21, 2011.
PCT/EP2010/068627 filed Dec. 1, 2010 Written Opinion dated Apr. 21, 2011.
PCT/EP2011/071489 filed Dec. 1, 2011 International Search Report dated Mar. 6, 2012.
U.S. Appl. No. 12/545,409, filed Aug. 21, 2009 Non-Final Office Action dated Apr. 13, 2012.
U.S. Appl. No. 12/650,863, filed Dec. 31, 2009 Non-Final Office Action dated Jun. 8, 2012.
JP 2011-523429 Office Action dated Jul. 17, 2013.
PCT/EP2008/064036 filed Oct. 17, 2008 International Preliminary Examination Report dated Apr. 20, 2010.
PCT/EP2008/064036 filed Oct. 17, 2008 Search Report dated Jan. 22, 2009.
PCT/EP2008/064036 filed Oct. 17, 2008 Written Opinion dated Jan. 22, 2009.
U.S. Appl. No. 12/545,409, filed Aug. 21, 2009 Final Office Action dated Nov. 20, 2013.
U.S. Appl. No. 12/545,409, filed Aug. 21, 2009 Non-Final Office Action dated Apr. 29, 2013.
U.S. Appl. No. 12/650,863, filed Dec. 31, 2009 Advisory Action dated Dec. 31, 2012.
U.S. Appl. No. 12/650,863, filed Dec. 31, 2009 Final Office Action dated Oct. 11, 2012.
U.S. Appl. No. 12/738,568, filed Apr. 16, 2010 Advisory Action dated Jun. 10, 2013.
U.S. Appl. No. 12/738,568, filed Apr. 16, 2010 Final Office Action dated Mar. 29, 2013.
U.S. Appl. No. 12/738,568, filed Apr. 16, 2010 Non-Final Office Action dated Nov. 2, 2012.
U.S. Appl. No. 12/958,089, filed Dec. 1, 2010 Advisory Action dated Oct. 28, 2013.
U.S. Appl. No. 12/958,089, filed Dec. 1, 2010 Final Office Action dated Aug. 15, 2013.
U.S. Appl. No. 12/958,089, filed Dec. 1, 2010 Non-Final Office Action dated Mar. 14, 2013.
U.S. Appl. No. 12/958,123, filed Dec. 1, 2010 Advisory Action dated Oct. 17, 2013.
U.S. Appl. No. 12/958,123, filed Dec. 1, 2010 Non-Final Office Action dated Mar. 25, 2013.
U.S. Appl. No. 12/958,184, filed Dec. 1, 2010 Advisory Action dated Nov. 5, 2013.
U.S. Appl. No. 12/958,184, filed Dec. 1, 2010 Final Office Action dated Aug. 14, 2013.
U.S. Appl. No. 12/958,184, filed Dec. 1, 2010 Non-Final Office Action dated Mar. 14, 2013.
U.S. Appl. No. 12/958,220, filed Dec. 1, 2010 Advisory Action dated Nov. 5, 2013.
U.S. Appl. No. 12/958,220, filed Dec. 1, 2010 Final Office Action dated Aug. 13, 2013.
U.S. Appl. No. 12/958,220, filed Dec. 1, 2010 Non-Final Office Action dated Mar. 15, 2013.
U.S. Appl. No. 13/309,420, filed Dec. 1, 2011 Advisory Action dated Feb. 13, 2014.
U.S. Appl. No. 13/309,420, filed Dec. 1, 2011 Final Office Action dated Nov. 8, 2013.
U.S. Appl. No. 13/309,420, filed Dec. 1, 2011 Non-Final Office Action dated Apr. 15, 2013.
U.S. Appl. No. 12/958,089, filed Dec. 1, 2010 Non-Final Office Action dated Jun. 20, 2014.

(56) References Cited

OTHER PUBLICATIONS

U.S. Appl. No. 12/958,123, filed Dec. 1, 2010 Non-Final Office Action dated Jun. 11, 2014.

* cited by examiner

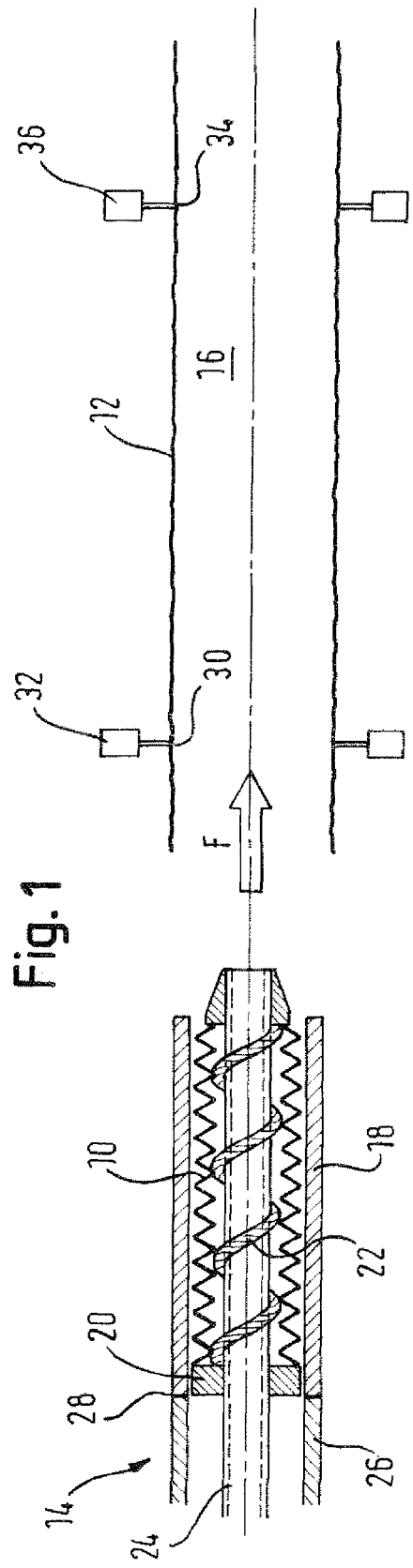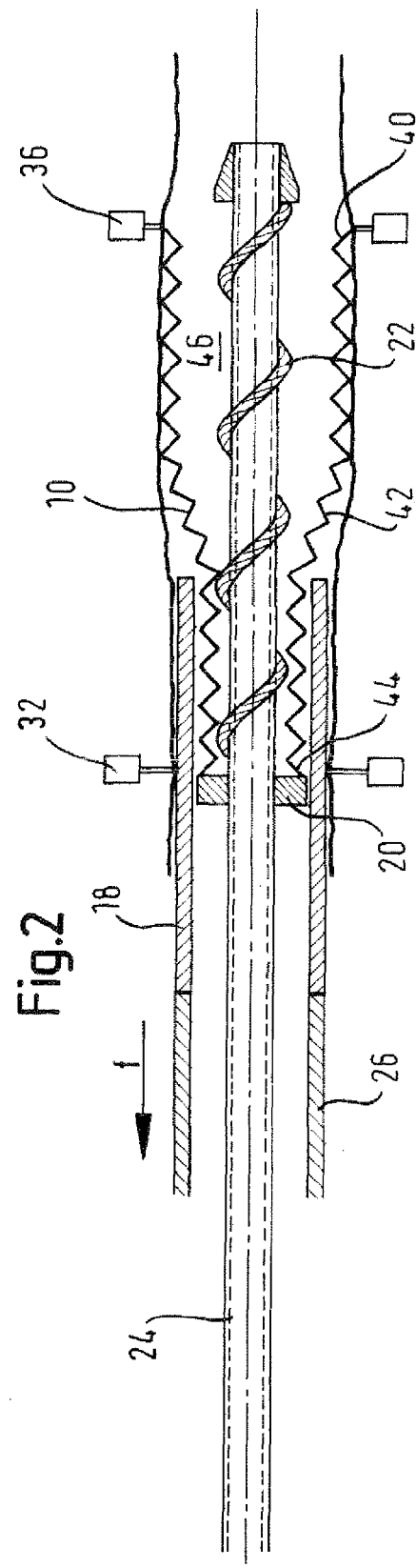

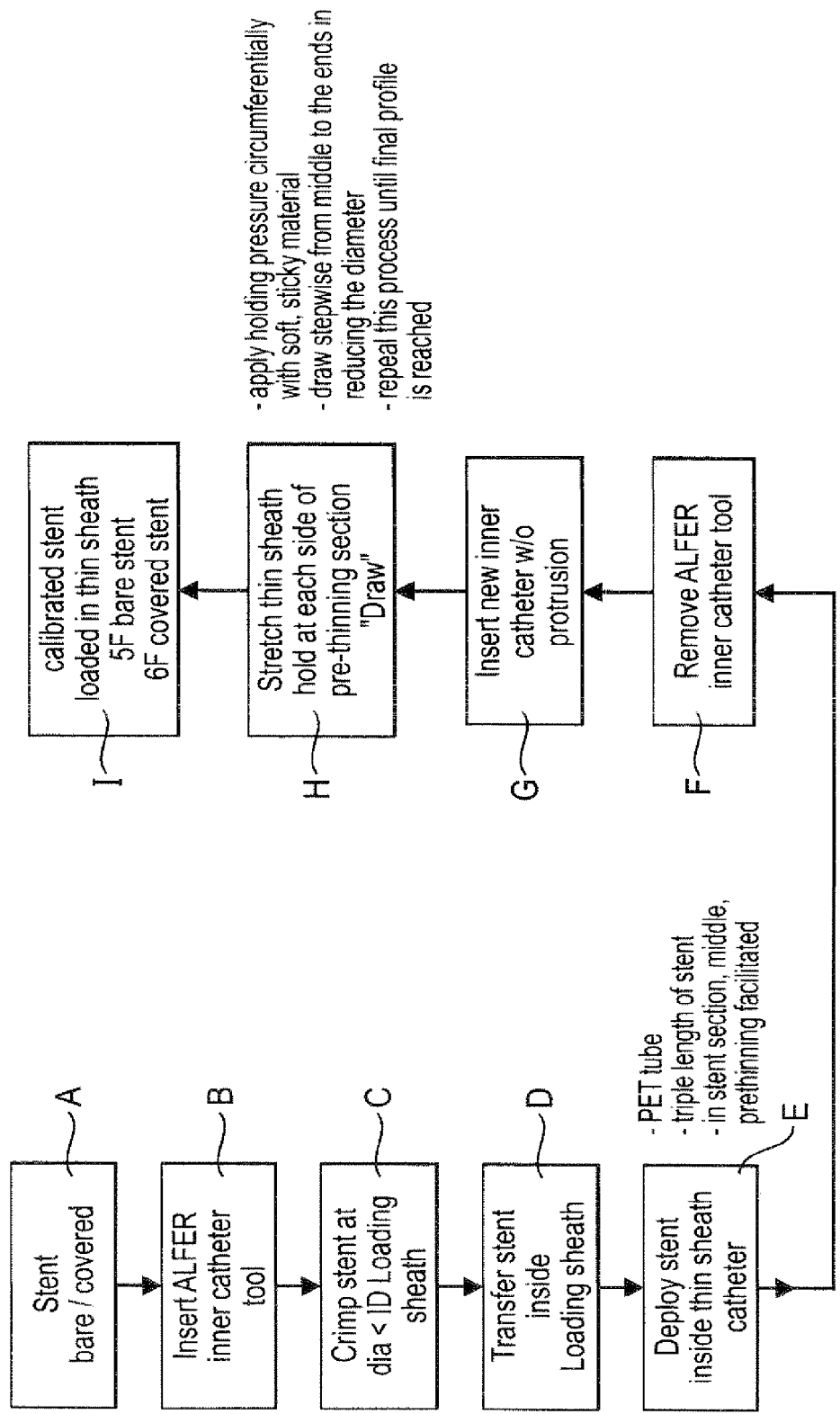

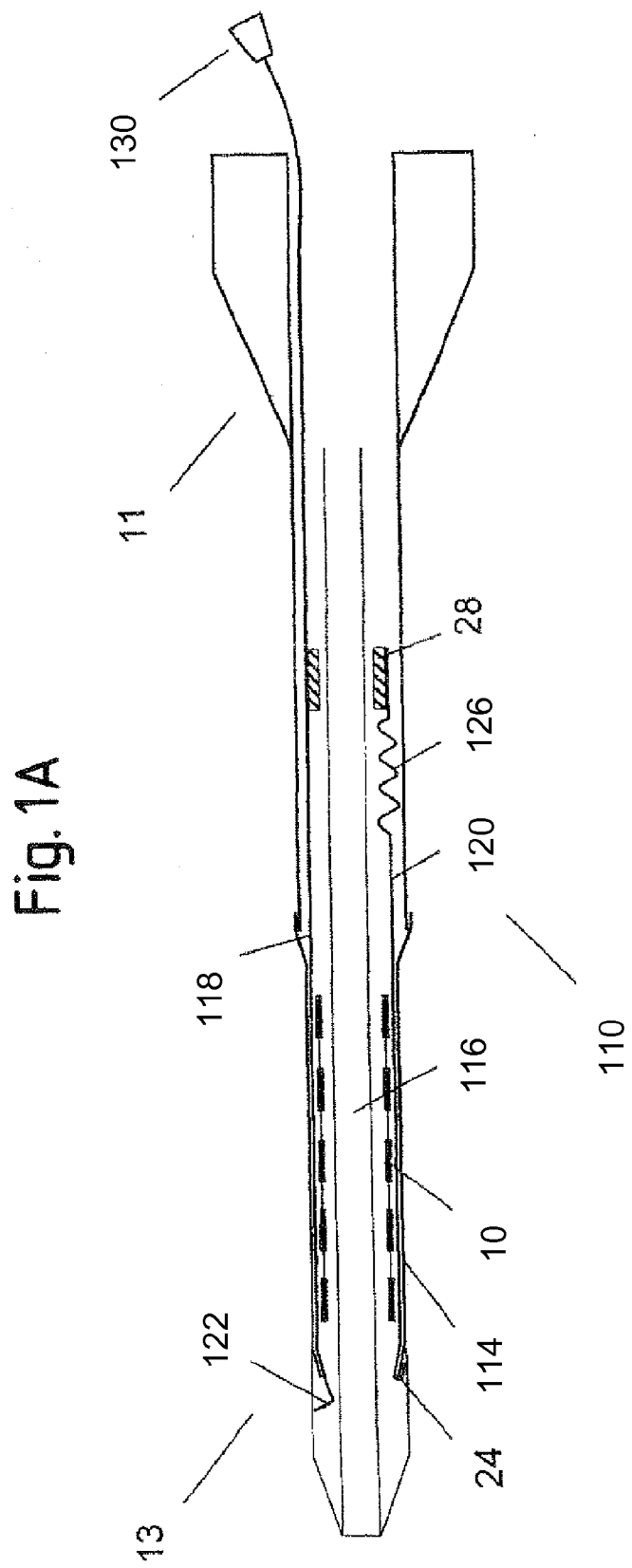

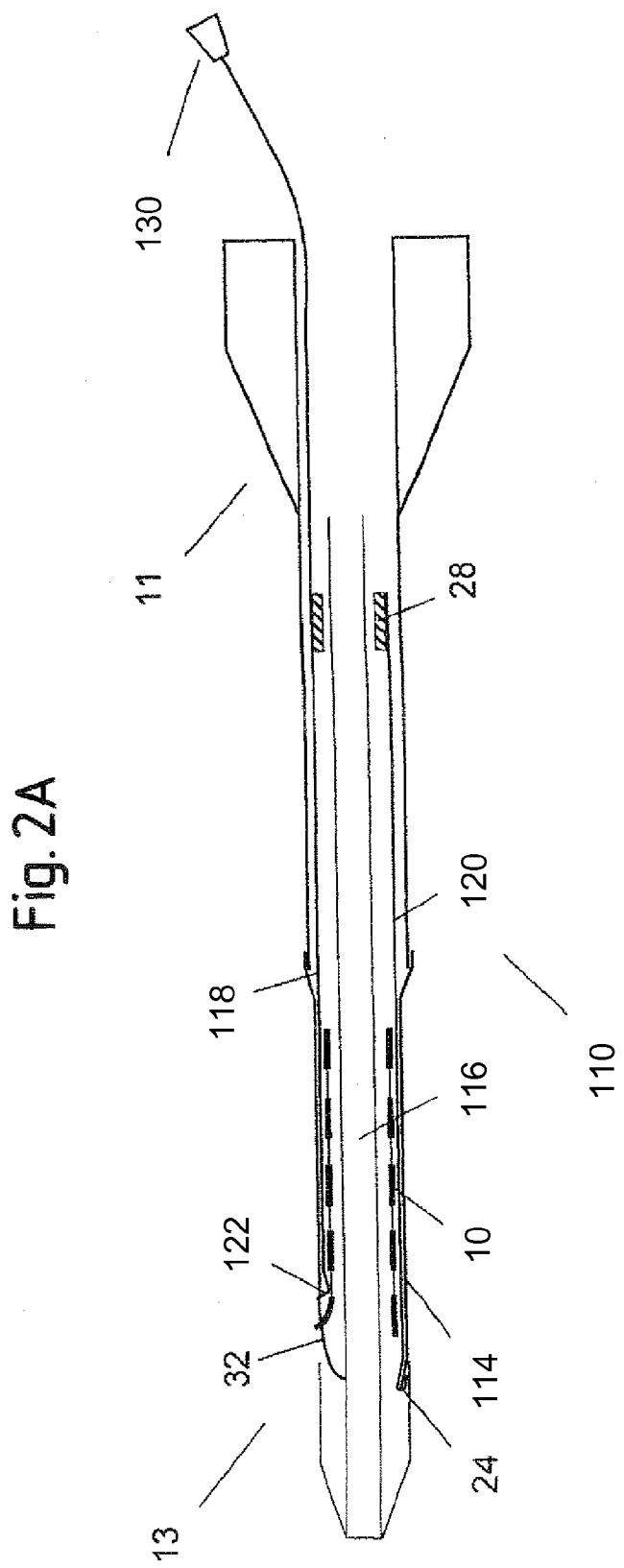

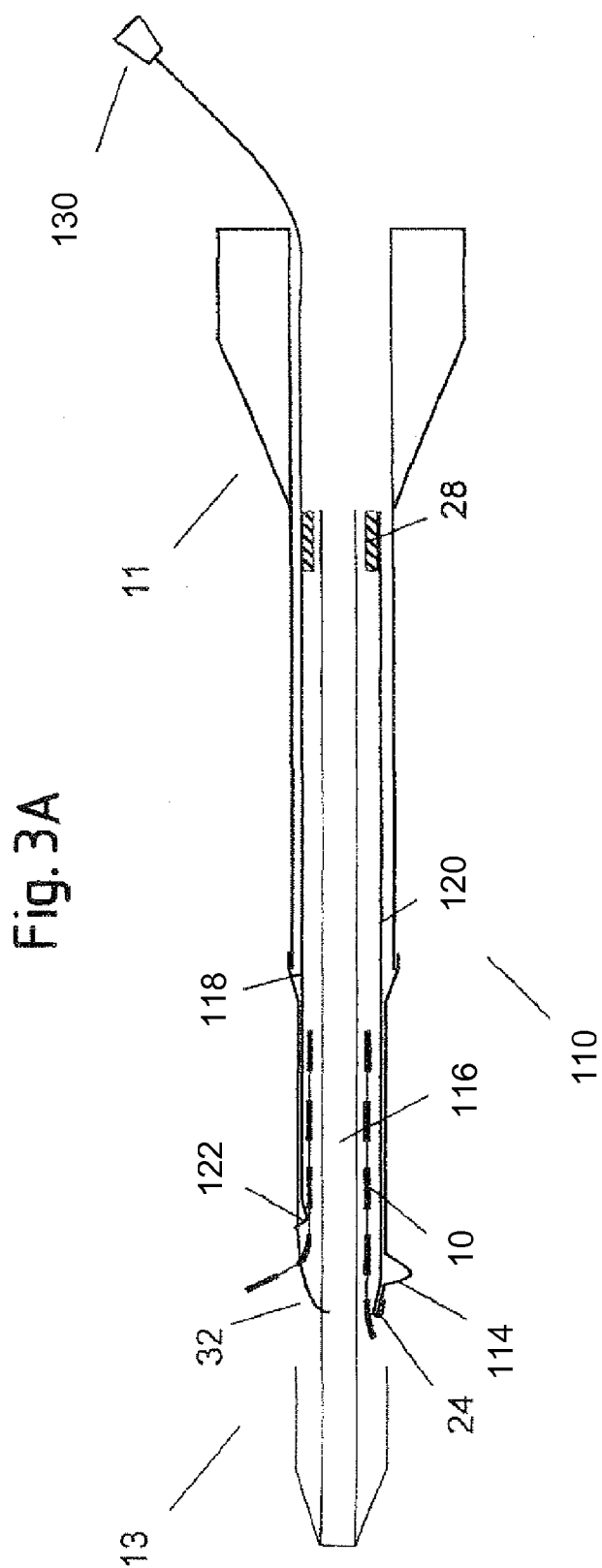

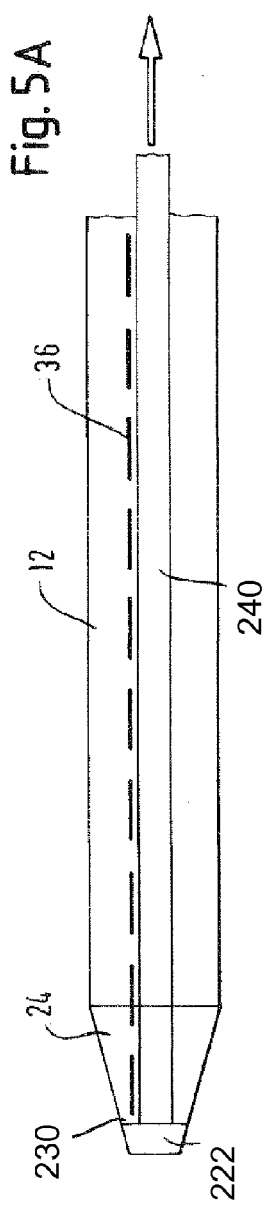

METHOD OF LOADING A STENT INTO A SHEATH

PRIORITY

This application is a U.S. national stage application under 35 USC §371 of International Application No. PCT/EP09/055592, filed May 8, 2009, claiming the benefit of priority to U.S. Provisional Application No. 61/090,772, filed Aug. 21, 2008. This application also claims the priority benefit of U.K. Patent Application No. 0815339.7, filed Aug. 21, 2008 and U.K. Patent Application No. 0808454.3, filed May 9, 2008. Each of which is incorporated by reference into this application as if fully set forth herein.

FIELD OF THE INVENTION

This invention relates to a method of loading a self-expanding stent into a delivery sheath that is part of a catheter for transluminal delivery of the stent to a stenting location in the body of a patient, with the stent being deployed at that location by removal from the stent of the constraint on its radial expansion that is provided up to that point by the sheath.

This invention relates to a delivery system for a self-expanding device for placement in a bodily lumen, the system comprising a sheath that confines the device to a radially compact delivery disposition until the device is to be released into the lumen.

Stent designers are succeeding in creating ever more sophisticated stents and stent grafts, for location in ever more sites in the body. There is consequently pressure on designers of stent delivery systems, to come up with designs for catheters that will reach ever more demanding requirements to convey such stents to the desired locations in the body.

The usual way to express a stent diameter is in units of "French." One French is one third of a millimeter. Thus, a stent delivery system with a passing diameter of "6 French" has an outside diameter of 2 mm. For a manufacturer of stents and stent delivery systems, a reduction of diameter from, say, 6 French to 5 French is a powerful technical advantage, and a great challenge for designers of stents and stent delivery systems. Measures that are capable of delivering even the tiniest reduction of the passing diameter of a stent delivery catheter might still be of considerable interest to such designers, provided the catheter is still as flexible, pushable and capable of reliable operations as a fatter catheter.

THE PRIOR ART

One way to release a stent from the constraint of a sheath is to run a slitter down the length of the sheath that surrounds the stent. See, for example, WO 01/08599, WO 93/17636 and WO 98/20812. However, a far more commonly used method is to pull the sheath proximally, relative to the stent, to release the stent progressively, starting at its distal end. See, for example, U.S. Pat. No. 5,833,694 Poncet. However, pulling on the sheath from its proximal end, will impose tensile stresses on the sheath material, in the length direction of the sheath. The sheath must therefore be physically strong enough, not only to resist the radially outward spring force that is coming from the self-expanding stent constrained within the sheath, but also the stresses to which the sheath is subject during the time that it is being pulled proximally, to release the stent. A force that tends to stretch a tube will also tend to reduce the diameter of that tube. A simple example is the toy called the "Chinese finger" that is in the form of a braided tube. The child slips it over his finger and then pulls the free end of the tube, causing the braiding to neck down, and grip tightly the finger within the lumen of the braided tube. Intuitively, one can appreciate that pulling on a sheath from the proximal end, when there is a self-expanding stent inside the lumen of the sheath, is a situation fraught with the possibility of unwanted additional, friction-generated loads that might be an impediment to smooth release of the stent.

One can appreciate that the wall thickness of the sheath makes a contribution to the totality of the passing profile of the stent delivery system, at least at the distal end of the catheter delivery system, in the "capsule" that contains the stent to be delivered by that system, for any such capsule is liable to be that portion of the length of the catheter that exhibits the greatest passing diameter. It is normally possible to devise a catheter delivery system in which the length of the catheter, the shaft, between the proximal end of the catheter held in the hand of the operator, and the distal end that exhibits the capsule containing the stent, will be of smaller passing diameter. Thus, designers are interested to reduce the wall thickness of the sheath surrounding the self-expanding stent, to the extent that is possible, consistent with safe operation of the system. It is of course intolerable for the sheath component to fail during deployment of the stent. The sheath component must be robust enough to withstand less than optimal handling of the stent delivery system, by medical practitioners, during placement of the stent.

For a statement of the background art relevant to the present invention, it is convenient to reproduce, immediately below, the description that was filed at the UK Patent Office on Oct. 17, 2007 by the present applicant with patent application number 07 203 27.6. That description reads as follows:

Catheter delivery systems are commonly used to introduce self-expanding endoprostheses in human or animal bodies and to advance them to the clogged or narrowed area. In the delivery system, the elongate endoprosthesis is held in a radially compressed state by a surrounding sheath to facilitate a smooth delivery. When the endoprosthesis has been placed in the destined area, it is expanded by withdrawing or opening up the sheath.

A catheter delivery system where the endoprosthesis is expanded by cutting open the sheath is disclosed in FR 2688688. In this system, three cutting wires are arranged equidistantly around the periphery of the endoprosthesis. Each wire runs from a proximal end of the catheter to a distal end, with the wire placed between the radially compressed endoprosthesis and the sheath in the region where the endoprosthesis is received, leaves the sheath at its distal end and runs back to the proximal catheter end along the outside of the sheath, so as to form a loop around the sheath wall. Both parts of the wires, in- and outside the sheath are guided parallel to one another and the overall six proximal wire ends are attached to a handle at the proximal end of the catheter. The sheath is opened by pulling the handle so that the distal ends of the three wire loops move proximally and cut through the wall of the sheath.

A catheter delivery system that uses only one cutting wire is disclosed in WO-A-01/08599. The wire consists of an inner pull element, running within the sheath, an outer pull element, running outside the sheath, and a separating element, located between the distal ends of the two pull elements at the distal end of the sheath. In order to expand the endoprosthesis, both pull elements are simultaneously pulled in a proximal direction, so that the separating element moves along the endoprosthesis towards the proximal catheter end and cuts through the sheath wall. Also belonging to the state of the art is WO2004/066809, which suggests to use a deployment line that is integral with a pull back sheath, to release an endoluminal device from inside the sheath.

In known catheter delivery systems that use a cutting mechanism to open up the sheath the cut open sheath is trapped between the expanded endoprosthesis and the wall of the vessel, once the expansion process is finished. To remove the sheath from the patient's body, it has to be pulled out from its proximal end. For the case of relatively large endoprostheses, such as oesophagus stents, where sheaths with thick walls can be used, this procedure is normally uncomplicated. However, problems arise when small-sized endoprostheses are required, for example to widen narrow blood vessels. In this case, the profile of the distal catheter end, comprising the endoprosthesis to be deployed, has to be strongly reduced, in order to facilitate accurate placement of the endoprosthesis and thus sheaths with thin walls have to be used. When such a thin-walled, cut open sheath is removed from the patient's body by pulling from its proximal end, the friction generated by the abluminal surface of the expanded endoprosthesis and the luminal surface of the vessel may cause either the sheath to tear, inhibiting its complete removal, or the endoprosthesis to move proximally with the sheath being pulled away from the axial position in the bodily lumen where it ought to be. Similar friction problems may arise even in traditional deployment methods, where an unslitted sheath is withdrawn from the endoprosthesis in the expansion process. When pulled from the proximal end, a thin-walled sheath may stretch along the direction of the pull, leading to a decrease of its radial diameter. This increases the friction caused between sheath and endoprosthesis, requiring a larger pulling force to move the sheath, similar to the known concept of the "Chinese finger trap". Eventually, the sheath may tear or the endoprosthesis may move away from the desired position.

It is an object of the present invention to advance stent delivery system design to achieve a smaller passing profile, consistent with simplicity of design and reliability of operation.

SUMMARY OF THE INVENTION

In accordance with one aspect of the present invention there is provided a method of loading a self-expanding stent into a delivery sheath that is by itself strong enough to preserve the stent in a radially compressed pre-deployment configuration, comprising the steps of:

i) compressing the stent to a relatively small diameter ii) providing a loading sheath with an inner diameter d1 iii) with the stent exhibiting an outside diameter of d2, where d2<d1, providing relative translational movement between the stent and the sheath, whereby the stent is accommodated within the lumen of the loading sheath;

iv) advancing the loading sheath, containing the stent, into the lumen of the delivery sheath; and v) deploying the stent into the lumen of the delivery sheath, by withdrawing the loading sheath while restraining the stent from axial movement out of the lumen of the delivery sheath.

In accordance with another aspect of the present invention, there is provided apparatus for installing a self-expanding stent in a sheath of a stent delivery catheter, the apparatus comprising a loading sheath with a lumen for containing the self-expanding stent, the apparatus deploying the stent into the delivery sheath by advancing into the lumen of the delivery sheath the loading sheath containing the stent, and then withdrawing from the lumen of the delivery sheath the loading sheath but not the stent.

According to a further aspect of the present invention there is provided a self-expanding stent (or stent graft) within the lumen of a delivery sheath of a stent delivery system, the delivery sheath being formed of polymeric material that has been cold drawn with the stent in situ, within the lumen of the sheath.

In a preferred embodiment of the method of the invention, the delivery sheath is subject to a lengthwise strain, after the stent has been installed in the lumen of the sheath, to draw down the inner diameter of the delivery sheath to a diameter d3, which is less than diameter d1.

In one preferred embodiment, the sheath is one which can be parted along a line extending axially the full length of the stent, to allow the stent to push the material of the longitudinally parted sheath of the way, during the radial expansion of the stent that occurs as the stent deploys into a bodily lumen. Conveniently, the sheath is made of polyethyleneterephthalate (PET) and typically has a wall thickness of 30 m prior to any drawing down of the diameter after placement of the stent in the lumen of the sheath.

It may be useful to design into the sheath a specific zone for initiation of the cold drawing strain, so that such strain spreads outwardly, progressively, along the length of the sheath, from the strain initiation zone, upon imposition on the sheath of the longitudinal stress needed to initiate the strain. Generally, it will be convenient to locate any such strain initiation zone somewhere between the opposite ends of the stent, such as midway along the length of the stent. The form of any such strain initiation zone could be a portion of the sheath that exhibits a reduced wall thickness.

Medical practitioners are seeking ever longer and more flexible stents. Such stents are correspondingly more problematic to handle, in such a way that no portion of the stent matrix is ever subject to a level of stress that prejudices the fatigue performance of the stent. Whereas short and robust stents tolerate being pushed from one end 1 long and flexible delicate stent designs are vulnerable to over-stressing, if not supported along their full length during loading into a sheath and during deployment out of that sheath. One way to provide support for a stent graft along the full length of the lumen of that graft can be found in the disclosure of Applicant's WO 2004/096091. Thus, for loading a stent or stent graft into the loading sheath of the present invention, it will generally be desirable to employ a tool that extends along the lumen of the stent and supports the stent matrix from within that lumen. Once the stent has been installed in the delivery sheath, designers have the option of leaving the tool in place, within the lumen of the stent, for making a contribution to the construction and operation of the delivery system for the stent or, in the alternative, removing the tool from the lumen of the stent, once the stent has been installed in the delivery sheath, and using for stent support during deployment of the stent some other component within the construction of the delivery system. Thus, an optional feature of the method of the present invention is the step of introducing into the lumen of the stent, as part of the process of installing the stent in the delivery sheath, a component of the delivery system that will deliver the stent to the stenting site within the body.

As for strategies for releasing the stent from the sheath, when the stent is deployed in the body at a stenting site, see Annex A that follows at the end and forms part, of this description.

As to the drawing down step, it is to be remembered that the sheath is of remarkably small wall thickness and so amenable to being cold-drawn in a simple manual operation in which the sheath is gripped in the hands of a skilled person. The left and right hands can simply be pulled apart from each other, simply to stretch the sheath in the portion of its length surrounding the stent. However, such procedures are not ideally suited to meet rigorous quality control procedures. It is therefore envisaged that the manually-achieved cold drawing step will, in real production, be replaced by a rigorously specified mechanical step so that the stretching process is performed always in the same way, for every delivery system produced. One envisages machine components that constitute first and second sheath grippers, one at each end of the sheath, beyond the respective end of the stent within the sheath, such grippers likely gripping the sheath all around the circumference of the sheath, probably with a high enough friction grip to hold the sheath ends securely, possibly with grip surfaces of silicone rubber material, with the first and second sheath grippers moving apart from each other in a controlled fashion, with sensors to provide control engineering feedback so that the sheath is always cold-drawn in the same manner.

Sheath delivery systems with a distal end capsule having an outside diameter of 6 French, or even less, are well within the contemplation of the inventors of the present invention.

The invention relates to a catheter delivery system for introducing and placing an endoprosthesis in a human or animal body. The catheter delivery system comprises a region in which to receive the endoprosthesis, an elongate sheath to surround the endoprosthesis in the region and a device for splitting the sheath along its length, to release the endoprosthesis from the region.

A main objective of the invention is to provide a catheter delivery system, where the sheath surrounding the endoprosthesis can be easily and reliably removed. In another objective, the invention aims to provide a catheter delivery system with a simplified sheath splitting mechanism that reduces the risk of damage to the body tissue when the sheath is cut open.

The invention provides a catheter delivery system for introducing and placing an elongate endoprosthesis in a human or animal body. The catheter delivery system has a proximal end and a distal end and comprises an elongate region at the distal end, in which to receive the endoprosthesis, an elongate sheath to surround the endoprosthesis in the region, and a device for splitting the sheath along its length, to release the endoprosthesis from the region where the endoprosthesis is received. The device for splitting the sheath comprises a first pull element with a proximal end at the proximal end of the delivery system and a distal end, comprising a splitting section for splitting the sheath. The first pull element extends to a distal end of the sheath at a distal end of the delivery system and can be pulled along the length of the sheath from the proximal end of the catheter delivery system. Further, the catheter delivery system comprises a second pull element that pulls the distal end of the sheath proximally during the movement of the first pull element along the length of the sheath. When the first pull element is pulled from the proximal end of the catheter delivery system, the splitting section moves from an original position at the distal end of the sheath towards the proximal catheter delivery system end, thereby splitting the sheath along its length. During this movement of the splitting section, the endoprosthesis expands from a radially compressed state to a radially expanded state in the region where the sheath has already been split. While the splitting section is opening up the sheath, the second pull element pulls the distal sheath end towards the proximal end of the catheter delivery system, thereby removing the sheath from the region where the endoprosthesis has expanded. Once the sheath is fully split, it can be completely removed from the distal end of the catheter delivery system, using the second pull element, and subsequently taken out of the patients body. The force exerted by the second pull element onto the sheath during the sheath removal process acts on the distal sheath end, so that stretching of the sheath along the pull direction (which may occur when the sheath is pulled from its proximal end) is avoided. Furthermore, when the sheath is starting to be removed, the endoprosthesis has only partly expanded. Thus, the area where the sheath is pushed against the vessel wall by the expanded endoprosthesis is smaller than for the case of a fully expanded endoprosthesis. This leads to a reduction of the frictional forces that have to be overcome in order to move the sheath. Hence, the force required to pull out the sheath is reduced, simplifying the removal process, and the sheath is exposed to a significantly lower level of stress. This is particularly important for the case of thin-walled sheaths, used for deployment of small endoprostheses in narrow blood vessels etc., that may easily stretch or tear, rendering a complete removal impossible or causing undesired movement of the endoprosthesis.

In a preferred embodiment, the first pull element is a wire. In this way, the pull element can be made with small lateral dimensions, so as to keep a reduced profile of the distal catheter delivery system end and sufficiently stable to avoid deformation or breakage when a pulling force is applied. The wire may have a round radial cross section or may be flattened along a circumferential direction of the endoprosthesis such as to have a ribbon-like shape. In the latter case, lateral movement of the wire along the periphery of the endoprosthesis during the pulling process is reduced and the wire is guided on the abluminal endoprosthesis surface. The splitting section may be attached to the distal end of the wire or may be formed as an integral part thereof. For example, the distal wire end may have a cross section that differs from that of the rest of its length, and that is particularly suited to split the sheath. Furthermore, the distal wire end may stand up in a radial direction of the endoprosthesis or form a hooked portion, so as to reliably catch and split the sheath.

In a further preferred embodiment, the second pull element is a wire. As for the case of the first pull element described above, in this way the second pull element can exhibit small radial dimensions whilst maintaining the required level of robustness. The radial wire cross section may be round or ribbon-like, whereby the latter configuration allows for a guided movement of the wire along the length of the endoprosthesis.

Preferably, the second pull element has a hooked portion at its distal end and the distal end of the sheath is received within the hooked portion. In this way, the distal sheath end can be securely attached to the distal end of the second pull element, without the need for any additional means of attachment that may increase the profile of the distal catheter delivery system end. For example, the distal end of the second pull element may be bent backwards, so as to form a hooked portion and the distal sheath end may be clamped within said portion, rendering the fabrication process cheap and simple.

Preferably, the distal end of the sheath is provided with a slit to receive the splitting section. Such a slit causes a reduction of the pulling force that is required to split the sheath at its distal end and thereby helps to prevent the formation of ripples in the sheath when the splitting section is moved towards the proximal end of the catheter delivery system. In addition, movement of the splitting section along the periphery of the sheath at the beginning of the splitting process is avoided, so that the sheath can be cut along a well-defined direction.

In another preferred embodiment, the sheath is at least partially covered with a hydrophilic coating. Such a coating effects a reduction of the frictional forces between sheath and luminal vessel surface, reducing the force required to remove the sheath.

Preferably, the second pull element runs between the endoprosthesis and the sheath in the region where the endoprosthesis is received. In this way, the second pull element can be prevented from moving across the body tissue of the inner vessel wall during the sheath removal process, avoiding possible damage to the patient's body or entanglement of the pull element. Furthermore, the pull element is securely guided between sheath and endoprosthesis when the sheath is removed.

In a further preferred embodiment, the first pull element and the second pull element are provided at positions that are substantially opposite each other on the circumference of the endoprosthesis. This arrangement allows for a maximum separation distance between the two pull elements and thus helps to avoid possible entanglement of the two components. Furthermore, when the distal end of the sheath is pulled towards the proximal catheter delivery system end, the force applied to the sheath is evenly distributed between the two parts of the split sheath portion that lie on opposite sides of the cut in a circumferential direction of the endoprosthesis. Thus, a smooth and uniform sheath removal can be achieved. In order to ensure said opposite arrangement of the two pull elements, a slit for receiving the splitting section may be placed opposite the position where the distal sheath end is secured to the second pull element.

In yet another preferred embodiment, the first pull element and the second pull element are coupled to each other by a coupling mechanism in such a way that, when the first pull element is pulled from its proximal end, also the second pull element is pulled via the coupling mechanism. In this way, the movement of the splitting section and the distal sheath end relative to each other is controlled by the coupling mechanism, ensuring a smooth sheath removal process. The surgeon only has to pull the first pull element, so that the operation of the delivery system is greatly simplified and any complications due to wrong use of the system are largely avoided. Furthermore, the coupling mechanism may be formed in a way that it ensures opposite positions of the two pull elements on the circumference of the endoprosthesis, as described above. For example, the coupling mechanism could be a ring-shaped object, with the two pull elements attached on opposite sides on its circumference.

Preferably, when the first pull element is pulled from its proximal end, both the distal end of the first pull element and the distal end of the second pull element move towards the proximal end of the catheter delivery system, with the distal end of the second pull element lagging behind the distal end of the first pull element by a predetermined distance, so that first the separating section starts separating the sheath and then the distal end of the sheath is pulled towards the proximal end of the catheter delivery system by the second pull element. Such a configuration can be achieved, for example, by making the second pull element longer than the actual distance between the position where it is secured to the distal sheath end and the position where it is attached to the coupling mechanism. This excess length is compensated for by arranging the second pull element in a wavy or undulating structure close to its proximal end. When the first pull element is pulled, the pulling force is transmitted to the second pull element via the coupling mechanism. While the splitting section is moved towards the proximal catheter delivery system end, the proximal end of the second pull element moves in the same direction, thereby straightening said wavy structure. This means that, although the proximal end of the second pull element moves, its distal end remains in its original position or, in other words, the system is in "lost motion". Once the wavy portion of the second pull element is fully straightened, the distal sheath end is pulled towards the proximal catheter delivery system end. The lag between the splitting section and the distal sheath end is defined by the excess length of the second pull element, and can thus be easily adjusted in the fabrication process.

In this way, it can be ensured that the splitting section starts splitting the sheath before the distal sheath end is pulled out, towards the proximal end of the catheter delivery system. The lag between the two components defines the length along which the sheath is split before it is starting to be removed and thus also substantially sets the length over which the endprosthesis expands prior to the sheath removal process. Hence, the lag should be set large enough to warrant that the sheath splitting process is initiated before the sheath removal process, yet small enough to ensure that a sufficiently small of the endprosthesis has expanded, to allow smooth removal of the sheath.

Preferably, a lag of a few millimeters is chosen, for example 5 mm.

In another preferred embodiment, the endoprosthesis comprises a stent. The invention allows for the use of very thin-walled sheaths, avoiding any complications in the sheath removal process, and is thus particularly useful for delivering endoprostheses with a small radial diameter, such as vascular stents. The distal end profile of the catheter delivery system can be reduced to ensure precise positioning of the stent in the patient's body and once in its desired place, the stent can be controllably expanded.

In yet another preferred embodiment, the endoprosthesis comprises a self-expansible stent. The stent expansion and sheath removal process can be controlled and coordinated by adjusting the lag between splitting section and distal sheath end, as described above. In particular for small self-expansible stents, the catheter delivery system of the invention offers a significant improvement over the traditional method of stent delivery, where the sheath is withdrawn from its proximal end. This procedure may cause thin-walled sheaths to stretch or tear, thereby limiting the minimum sheath wall thickness and thus also the minimum achievable distal end profile of the catheter delivery system. Nevertheless, the invention may be useful even with prostheses that are not self-expanding, such as the well-known balloon-expandable stents.

Preferably, the stent has an elongate shape, can be in a radially expanded and in a radially compressed state, and has a radial diameter of 6 French or less when it is in the radially compressed state and a radial diameter of 4 mm or more when it is in the radially expanded state. As described above, the catheter delivery system of the invention allows for a significant reduction in radial stent diameter, thus considerably extending the range of use of the apparatus.

Preferably, the sheath is made from PET. Such sheaths can be formed with sufficiently thin walls, while maintaining the required level of robustness to safely retain the endoprosthesis. PET is known for its low compliance. A balloon of PET behaves like a paper bag. In general, low compliance polymers are likely to be more useful in the present invention than higher compliance polymers like polyethylene. In addition, PET sheaths are cheap and easy to manufacture.

Furthermore, the endoprosthesis can be easily loaded into such a PET sheath, simply by placing the endoprosthesis inside the sheath and cold drawing the sheath in such a way as to axially strain it sequentially, preferably from the distal to the proximal end of the sheath. In this way, the sheath is stretched in its axial direction and the radial sheath diameter is adjusted by controlling this stretching process.

In a second aspect, the invention provides another catheter delivery system for introducing and placing an elongate endoprosthesis in a human or animal body. The catheter delivery system has a proximal end and a distal end and comprises an elongate region at the distal end, in which to receive the endoprosthesis, an elongate sheath to surround the endoprosthesis in the region, and a device for splitting the sheath along its length, to release the endoprosthesis from the region where the endoprosthesis is received. The device for splitting the sheath comprises a pull element with a proximal end at the proximal end of the delivery system and a distal end, comprising a splitting section for splitting the sheath. The pull element extends to a distal end of the sheath at a distal end of the delivery system and can be pulled along the length of the sheath from the proximal end of the catheter delivery system. In the region where the endoprosthesis is received, the pull element is devoid of any structure outside the sheath and the distal end of the pull element is distal of a distal end of the endoprosthesis at a distal end of the catheter delivery system. In this way, it can be prevented that the pull element moves across the body tissue of the inner vessel wall during the sheath splitting process, thereby avoiding possible damage to the patient's body or entanglement of the pull element. If the pull element is retained between sheath and endoprosthesis, it is securely guided during the sheath splitting process.

The splitting section may be attached to the pull element at its distal end or may form an integral part thereof. For example, the splitting section could comprise a sharp edge, like a blade, to cut the sheath when moved along its length. However, in a different embodiment, the splitting section may include a blunt component or portion instead that has the shape of, for example, a ball, a wedge or a "humpback". The blunt component or portion has a larger thickness in the radial direction of the delivery system than the rest of the pull element. Thus, when said component or portion is moved along the length of the endoprosthesis, it induces extra tension in the sheath which is closely surrounding the endoprosthesis, causing the sheath to tear. This latter embodiment is particularly useful when the sheath is provided with a slit to receive the splitting section, reducing the force necessary to initiate the sheath splitting process. In this case, the splitting location is defined by the position of the slit and no sharp edges are present that might carry a risk of damage to the vessel wall tissue.

Furthermore, in the embodiment of the catheter delivery system of the second aspect of the invention illustrated in the appended drawings, only one pull element has to be pulled in order to split the sheath. This simplifies the use of the catheter delivery system and avoids the problems that may arise when more than one pull element is used, such as entanglement or an uneven distribution of pulling forces.

Use of only one pull element is particularly advantageous in combination also with the first aspect of the invention, namely the splitting device aspect. In this case, only one pull element has to be pulled in order to split the sheath and reliably remove it from the region of the endoprosthesis. Nevertheless, the present invention can also be embodied in devices which exhibit more than one pull element, distributed around the circumference of the sheath. More than four such pull elements around the circumference, however, is not preferred.

The present invention provides a delivery system as identified above, which includes an elongate pull element to be pulled proximally from its proximal end, which pull element is arranged radially inside the sheath for pulling preferentially on a pull zone on the circumference of the distal end of the sheath, thereby to tear the sheath progressively along a tear line running the length of the sheath, starting at the distal end of the sheath, to release the device from the confining effect of the sheath, progressively, beginning at the distal end of the device.

BRIEF DESCRIPTION OF THE DRAWINGS

For a better understanding of the present invention, and to show more clearly how the same may be carried into effect, reference will now be made, by way of example, to the accompanying drawings, in which:

FIG. 1 is a longitudinal axial section through a device for loading a stent into a delivery sheath;

FIG. 1A shows an axial cross section of a catheter delivery system according to a preferred embodiment in an initial position;

FIG. 2 shows the device of FIG. 1, but with the stent partially loaded in the sheath;

FIG. 2A shows an axial cross section of a catheter delivery system according to a preferred embodiment in a first intermediate position, where the sheath cutting process has started;

FIG. 3 is a flow diagram of method steps for installing a stent or stent graft within a sheath, in accordance with the present invention.

FIG. 3A shows an axial cross section of a catheter delivery system according to a preferred embodiment in a second intermediate position, where the sheath removal process has started.

FIG. 4A is a diametral longitudinal section through the distal end of a stent delivery system;

FIG. 5A is a section that is the same as FIG. 4, but shows only the sheath and elongate pull element of FIG. 4, for improved clarity;

FIG. 7A is a section corresponding to that of FIG. 4, but showing the system part way through the process of stent release.

DETAILED DESCRIPTION

Figure 6:
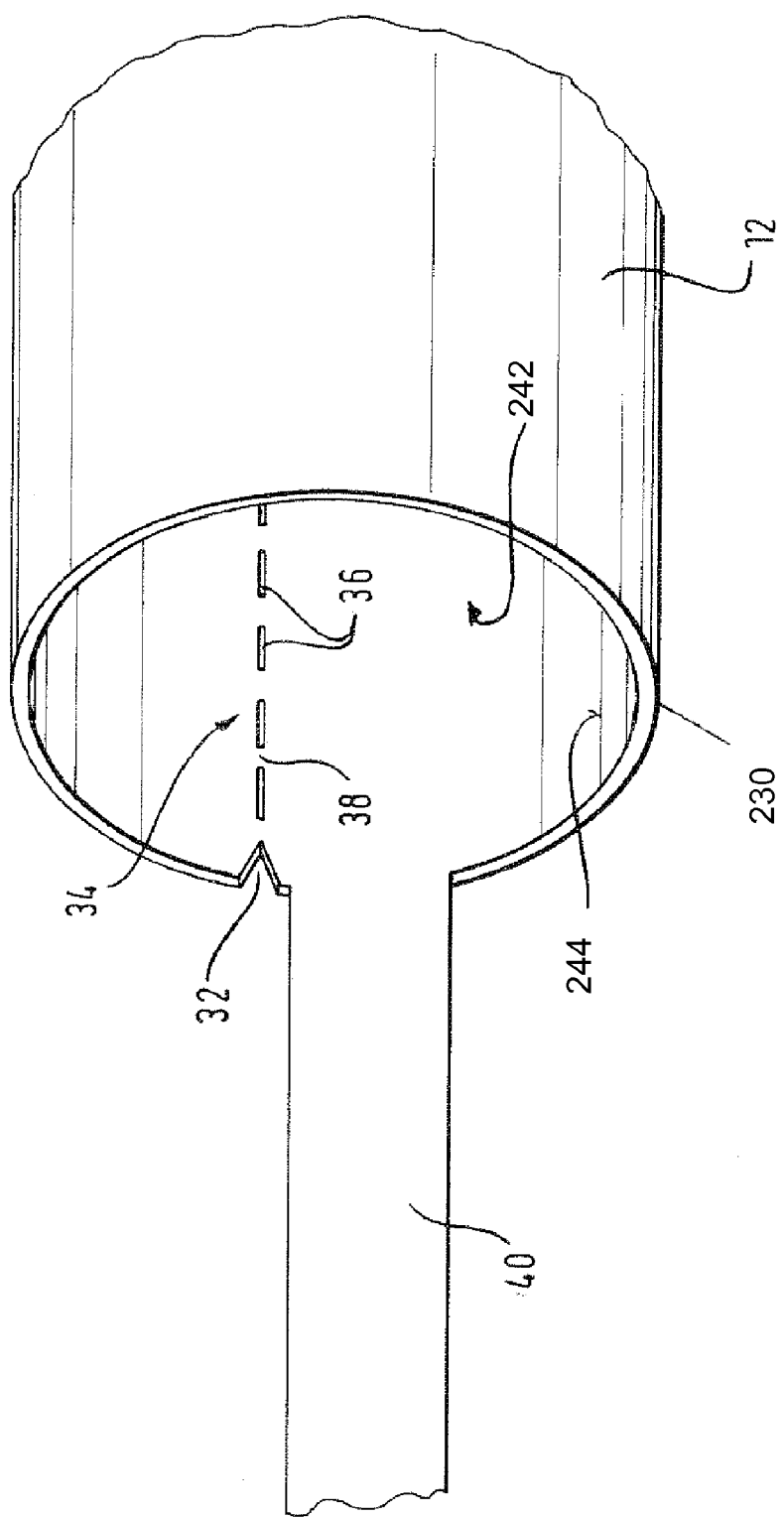
FIG. 6A is a view from the side, of the distal end of the sheath and pull element of FIG. 5.

FIG. 1 shows a crimped covered stent 10 ready for deploying from a loading sheath into a delivery sheath 12, by advancing the stent 10, in a loading tool 14 into the lumen 16 of the sheath 12, in the direction of arrow F.

The stent 10 is a radially self-expanding nickel titanium alloy stent covered in an ePTFE film. This covered stent is constrained by a loading sheath 18 in a radially compact disposition. The stent is installed in the loading sheath 18 by a "crimping" procedure known per se in which a jig (not shown) compresses the stent radially inwardly, down to its compact disposition, whereupon the stent 10 and the loading sheath 18 are moved relative to each other axially (usually by holding the sheath 18 stationary and translating the stent 10 into the lumen of the sheath 18).

Before the stent is crimped, there is inserted in its lumen a shaft 24 carrying a sequence of rings standing proud of the cylindrical surface of the shaft, or a spiral thread 22 running along the shaft. The covered stent is crimped down onto the shaft, whereupon the shaft can push the stent along its axis, supporting the stent all the way along the length of the stent 1 within its lumen. For more details, see the description herein with respect to FIGS. 1A-7A.

In accordance with the present invention, the stent 10 is then "deployed" into the lumen 16 of the delivery sheath 12. For that deployment, the confining sheath 18 is pulled proximally by a pulling tube 26 contiguous with the proximal end 28 of the loading sheath 18.

During this pulling, one restrains the shaft 24 from axial movement, which prevents the stent from moving axially with the retreating loading sheath 18, so that the sheath remains in the desired location, inside the delivery sheath 12.

The delivery sheath 12 is of rather thin-walled PET tubular material. It is gripped at its proximal end 30 by an annular gripper chuck 32 and gripped at its distal end 34 by a similar annular gripping chuck 36, so that the two chucks 32 and 36 hold the opposite ends 30 and 34 of the delivery sheath 12 at a desired distance apart while the stent is deployed into the sheath lumen 16.

This deployment process can be seen, partially completed, in FIG. 2 of the drawings, where like reference numerals identify the same components as are shown in FIG. 1. It will be appreciated that the loading sheath 18 has moved proximally, in the direction of arrow f, relative to the stent and to the stent pusher annulus 20, thereby releasing the stent 10 into the lumen 16 of the delivery sheath 12 progressively, starting at the distal end 40 of the stent, through a radially expanding portion 42 of the stent that travels the full length of the stent, from the distal end 40 to the proximal end 44 of the stent, not yet free of the confining loading sheath 18 as shown in FIG. 2. Once the full length of the stent 10 is clear of the loading sheath 18, the full radially outwardly directed stenting force from the stent 10 is carried by the delivery sheath 12, and the lumen 46 of the stent is big enough for simple proximal withdrawal from that lumen of the tubular element 24 of the loading machine.

As explained above, the stent 10 is now radially confined within the delivery sheath 12 and can be regarded as a precursor for a "capsule" for placement at the distal end of a catheter delivery system for the stent.

FIG. 1A shows an axial cross section of a catheter delivery system 110 according to a preferred embodiment in an initial position before expansion of the endoprosthesis. The delivery system 110 has a proximal end 11 and a distal end 13, comprising an elongate region 116 where a vascular self-expansible stent 10 is received. The stent 10 is surrounded and held in its radially compressed state by a sheath 114 made of PET. Further, the delivery system 110 comprises a first 118 and a second 120 pull element that both consist of a metallic wire and run between the stent 12 and the sheath 114 in the region 116 where the stent 10 is received. In this region 116, the wires of both pull elements 118, 120 are flattened along a circumferential direction of the stent 122, so as to have a ribbon-like shape. The first pull element 118 has a splitting section 122 at its distal end that is formed by a wire portion standing up in a radial direction of the delivery system 110 and a handle 130 attached to its proximal end for pulling the pull element 118 in a direction towards the proximal end 11 of the delivery system 110. The second pull element 120 has a hooked portion 24 at its distal end that is clamped onto the distal end of the sheath 114, so as to provide a secure attachment. At its distal end, the second pull element 120 is attached to a metallic ring that is itself attached to the first pull element 118 and serves as a coupling mechanism. The two pull elements 118, 120 are arranged opposite each other on the circumference of the stent 10 and secured in this configuration by the coupling mechanism 28. Close to the coupling mechanism 28, the second pull element 120 has an undulating portion 126. For stent 10 deployment, the first pull element 118 is pulled towards the proximal end 11 of the delivery system 110, using the handle 130. This causes the splitting section 122 to move along the length of the stent 10 in the same direction, thereby splitting the sheath 114 along its length as is shown in FIG. 2A. In the section 32 of the distal catheter region 116, where the sheath 114 has already been split, the stent 10 starts to expand radially. Simultaneously the coupling mechanism 28 is moved towards the proximal end 11 of the delivery system by the first pull element 118, thereby pulling the distal end of the second pull element 120 in the same direction. FIG. 2 shows an axial cross section of the catheter delivery system 110 of FIG. 1A in a first intermediate position, where the second pull element 120 has been fully straightened and the undulating portion 126 has disappeared. However, the hooked portion 24 of the second pull element 120 is still in its initial position. Thus, the sheath 114 has been partially split and the stent 10 has started expanding in the split region 32, but the sheath 114 removal process has not started yet. When the first pull element 118 is pulled further towards the proximal delivery system end 11, the hooked portion 24 starts pulling the sheath 114 proximally from its distal end as can be seen in FIG. 3A, showing the catheter delivery system 10 of FIGS. 1A and 2A in a second intermediate position. Once the sheath 114 is split along its whole length, the stent 10 fully expands into its radially expanded state. Subsequently, the sheath 114 is completely removed from the region 116 where the stent 10 is received, by further pulling the first pull element 118. Then the catheter delivery system 110, including the split sheath 114, can be taken out of the patient's body.

The present embodiment represents an example for a combination of the two aspects of the invention and illustrates the advantages of such a configuration: sheath splitting and removal can be performed reliably and quickly in one work step, simply by pulling a single pull element 118; the danger of damage to body tissue due to moving elements is minimized; entanglement of different pull elements is avoided; and the distal end profile of the catheter delivery system 110 can be reduced, allowing accurate placement and controlled deployment even of very small endoprostheses.

The process is presented in a block diagram, in drawing FIG. 3. However, FIG. 3 identifies further steps of the manufacturing process. The sequence of steps in FIG. 3 is identified by references A to I and we have the following comments on these process steps.

Step A is the step of providing the stent or stent graft of choice. A bare stent is one without any covering. A stent graft is a covered bare stent and the covering is typically of expanded polytetrafluoroethylene (ePTFE) but other covering materials are known to those skilled in the art.

Step B is the step of installing in the lumen of the chosen stent an inner catheter tool and the one preferred by the present Applicant is that described in its earlier publication WO 2004/096091 which goes by the acronym "ALFER".

Step C is the step of crimping the stent to bring the outside diameter of the chosen stent down to one that is small enough for loading the crimped stent into the chosen loading sheath 18. Next, step D, the crimped stent is translated axially into the lumen of the loading sheath 18. Then, the loading sheath carrying the stent is translated (as explained in FIGS. 1 and 2) into the lumen 16 of the delivery sheath 12 and the loading sheath 18 is withdrawn in order to deploy the stent into the delivery sheath. As noted on FIG. 3, the delivery sheath 12 is conveniently a PET tube having a length about three times that of the stent, with a pre-thinned zone in the PET tube located midway along the length of the stent in the lumen of the PET tube.

Once the stent is deployed, the inner catheter loading tool can be removed, step F, from the lumen of the deployed stent. At this point, step G, any desired component of the catheter delivery system which is to be located in the lumen of the stent can now be introduced into that lumen.

Having prepared the stent lumen, the delivery sheath can now be cold-drawn, lengthwise, to impose substantial strain on the material of the delivery sheath. This strain will have the effect of reducing the wall thickness of the delivery sheath, and generating hoop stresses within the delivery sheath being cold-drawn, which hoop stresses will tend to compress the stent inside the lumen of the delivery sheath, and therefore marginally reduce its diameter. The FIG. block diagram carries notes in relation to this step H of the process. These notes teach to use a soft sticky material to grip the delivery sheath for achieving the cold-drawing strain. That strain is conveniently imposed on the sheath stepwise, commencing at the midpoint of the length of the sheath and repeating the cold-drawing process, stepwise, until a final desired outside diameter profile is achieved for the sheathed stent. Thus, in the final step of the process, the stent-bearing capsule is ready for combining with other components of the catheter system that is to deliver the stent to the site of stenting in the body of a patient.

Referring first to drawing FIG. 4A, a self-expanding nickel-titanium shape memory alloy stent 10 is confined within a sheath 12 in a catheter device 214 which constitutes a transluminal delivery system for the stent 10, that has a tapered atraumatic distal tip 216. The catheter has a shaft 218 that defines a bore 20 for a guidewire along which the catheter delivery system may be advanced until its distal end zone carrying the zone 10 is in the desired site of stenting.

Carried on the shaft 218 at its distal end zone is a distal tip element 222 that receives an inwardly tapered end portion 24 of the sheath 12 surrounding the stent. At the proximal end of the stent 10 is a pusher annulus 226 that is also a radiopaque marker and is fixed to the outside surface of the catheter shaft element 218. When the time comes to deploy the self-expanding stent 10, the hoop stresses in the sheath 12 surrounding the stent 10 have to be released, so that the stent 10 can expand radially into the stenting site within the bodily lumen. Conventionally, this is accomplished by simply pulling the sleeve 12 proximally until it slides over the stent 10, withdrawing proximally relative to the stent, to release the stent progressively, starting at its distal end, into the bodily lumen. However, with the present invention, the stent release mechanism is quite different, as will now be explained with reference to FIGS. 5A and 6A of the drawings.

First looking at FIG. 6A, we see distal end 230 of the sheath 12, with a circumference that includes a short slit or "nick" that will serve as a tearing initiation point on the circumference of the distal end 230. Extending proximally from the tearing initiation site 32 is a line of weakness 34 that is created by a line of elongate perforations 36, co-linear and spaced from each other to provide a line of weakness running all the way from the tearing initiation site 32 to the proximal end annulus of the sheath 12. The residual material 38 in the gaps between the slits 36 is sufficient to maintain the hoop stresses and integrity of the sheath 12 until the moment when it is desired to release the stent by tearing down the line of weakness by rupturing the sequence of material bridges 38 between adjacent slits 36.

To accomplish this task, there is employed a pull element 240 which is shown in FIG. 6A extending distally away from the end annulus of the sheath 12 but which is in actual use of the device folded inside the open end 242 of the sheath 12 so that it lies sandwiched between the stent 10 and the inside surface 244 of the sheath 12, running the full length of the stent 10 and extending further, proximally, beyond the pusher annulus 226. Not visible in the drawings, but nevertheless indicated by reference 46, is a coating of hydrophilic material on the major surfaces of the sheath 12. Not shown in the drawings (but those skilled in the art will be able to develop the details for themselves) is the structure of the catheter proximal of the pushing annulus 226. The catheter shaft might be of the "over the wire" variety or of the "rapid exchange" variety, depending on the length of the guidewire lumen. There needs to be in the shaft a pushing member (conveniently a tube) to convey the endwise compressive stress to the pusher 226. Further, there needs to be a pull element (conveniently a pull wire) to deliver to the pull element 40 the necessary tensile stress to tear the sheath. Conveniently, the connection between the pull wire running the length of the catheter shaft, and the pull element 40 that extends from proximal of the pusher annulus 226 to the distal end of the sheath 12, is an annular element that slides on the shaft 218 and conveniently serves as a radiopaque marker of the progress of the pulling element 240 as it progresses proximally release of the stent.

Alternatively, the pull element might extend proximally the full length of the catheter. Proximal of the stent, it could be twirled into a strand with a helical trace on its cylindrical surface, that extends along a pull wire lumen in the catheter shaft.

Turning now to FIG. 7A, we can observe the stent release process with a "snapshot" of the process in progress, with a distal portion 50 of the stent 10 already released from the radially confining effect of the sheath 12, as the pull element 240 moves proximally relative to the stent 10 lying radially inside it and the sheath 12 laying radially outside it. This proximal progress of the pull element 240 draws into the annulus between the untorn sheath 12 and the stent 10 the distal-most portion of the sheath 12, that has already been parted along the line of weakness 34, thereby releasing hoop stresses in the distal-most portion of the sheath 12 and allowing it to relax distally outwardly, even as it finds itself being pulled proximally into the annulus between the untorn sheath 12 and the stent 10. This distal-most portion of the sheath is indicated by reference 52 in FIG. 7A. We can already see in FIG. 7A that the sheath no longer extends all the way to the distal end of the stent 10, precisely because the proximal movement of the pull element 240 causes the sheath to double back on itself, radially inwardly. It should be remembered that the inherent stiffness of the sheath is remarkably low, because the PET material of which the sheath is formed has a high modulus of elasticity and high physical strength so that its wall thickness can be remarkably small. Once the hoop stresses in the distal-most portion of the sheath are relieved, this distal portion of the sheath is remarkably compliant and amenable to the creasing and folding that is going to occur when a full 360° circumference is pulled proximally by a pull element 240 that extends around only a portion of that circumference adjacent to the line of weakness where the sheath is progressively rupturing from its distal end to its proximal end.

By the time the tearing of the sheath has progressed as far as the proximal end of the stent, the entire length of the stent will have expanded radially into position in the bodily lumen to be stented, and any portion of the sheath 12 that lies sandwiched between the stent and the bodily lumen will be only at the zone of the stent closest to its proximal end and will therefore be relatively easily withdrawn from between the stent and the bodily lumen, as soon as the stent delivery system as a whole is pulled proximally away from the deployed stent.

The present invention represents another step along the path of design of delivery systems for devices such as self-expanding stents and stent grafts, at a location within the body that is difficult to reach, and challenging in terms of the small dimensions of the stenting location. A sheath that confines the self-expanding stent radially, until the moment when it is to be released into the bodily lumen, should be strong enough to confine the stent, but with a wall thickness as thin as can be achieved, for maximum flexibility and maximum capability to advance to the site of delivery through narrow and tortuous bodily lumens. The inventive concept, of releasing the stent by pulling the sheath proximally while tearing the sheath progressively, along a tear line that begins at the distal end of the sheath, fits with the concept of progressive release of a self-expanding stent commencing at its distal end. Furthermore, the idea of using a pull element to pull proximally the distal end of the sheath, during the progressive release of the stent, fits with the idea of pulling the sheath back proximally, away from its location between the stent and the bodily lumen to be stented, before the stent has fully expanded radially and pressed itself into the tissue wall of the lumen, thereby facilitating proximal withdrawal from the stenting location of the stent delivery system, including the sheath that has been torn by the pull element. Readers will appreciate that the tearing induced by pulling on the pull element is assisted and encouraged by the consequent radial expansion of the stent, progressively, beginning at its distal end, the hoop stresses in the sheath, being generated by the stenting forces within the radially expanding stenting rings of the stent escaping from the sheath.

The inventor envisages percutaneous placement of self-expanding stents or stent grafts with a delivery system that advances over a 35 thou (0.035 inches) diameter guidewire, the delivery system envisaged having in preferred embodiments a passing diameter of as little as 5 French (1 French=⅓ mm) or even less, for a bare stent prosthesis, or 6 French (or even less) for a covered stent with the potential to expand after placement to a diameter of up to 12 mm.

Furthermore, readers will appreciate that a stent release mechanism that works by tearing and pulling a sheath offers the potential to deploy stents and stent grafts that are axially longer than conventional. Indeed, one envisages deploying with the present invention stents and stent grafts having lengths of up to around 300 mm (or even longer).

With the pull element serving to drag material of the sheath into the annulus between the stent and the untorn sheath, it will generally be beneficial to provide the sheath material with a hydrophilic coating which will attract water molecules to the coating to serve as a lubricant, even while the pull element pulls the torn sheath proximally over the stent until the stent is fully released.

A preferred material for making the sheath is polyethylene phthalate-PET-that is cold-drawn over the prosthesis mounted in a catheter delivery system. Such a PET sheath can be sequentially axially stretched by the cold-drawing process, starting from the distal end of the self-expanding device and moving through to the proximal end of the device, to control the radial shrink diameter and final profile. Advantageously, the distal tip of the sheath is drawn down to an outside diameter that is substantially smaller than the outside diameter of the sheath where it embraces the self-expanding device, in order that the sheath shall itself define the outside of an atraumatic tip section for the delivery system as such.

The embodiment that is for the time being preferred has a single line of weakness in the wall thickness of the sheath, that extends lengthwise along the sheath, starting from a tear initiation point on the circumference of the distal end of the sheath and running to the proximal end of the sheath, the line of the line of weakness being near to the pull zone at the distal end of the sheath. Thus, pulling on the elongate pull element will impose tearing forces on the sheath at the tear initiation point of the line of weakness near to the pull zone, initiating a tearing of the sheath along the line of weakness, that progresses as the pull element is pulled and withdrawn proximally. Nevertheless, embodiments are envisaged in which there are two lines of weakness, parallel to each other, and one each side of the pull zone so that pulling on the elongate pull element pulls a strip of the sheath proximally, with the pull element, but not the remainder of the circumference of the sheath that is the arc of the circumference of the distal end of the sheath on the other side of the sheath circumference from the pull element, that complements the arc between the two tear initiation points and shared with the pull element.

The or each line of weakness is conveniently provided as a line of perforations through the wall thickness of the sheath and, preferably, each line of weakness terminates, at its tear initiation point, in a slit.

It is envisaged that the pull element will be contiguous with the sheath, monolithic with the sheath, but not cold-drawn in the same way as the sheath. Although such a pull element could be a band of the sheath material that has a width of as little as around 1 mm, band widths preferred for the time being are widths that take up at least 50% of the circumference of the sheath, so that pulling on the pull element directly pulls proximally into the annulus between the sheath and the self-expanding device an arc of the circumference of the sheath that is more than half of the circumference. It will be appreciated that such embodiments will be effective in pulling a large proportion of the material of the sheath progressively proximally as the self-expanding device expands out of the torn distal end of the sheath, to leave a minimum of the sheath material trapped between the expanded stent {or other device) and the tissue of the bodily lumen being stented.

An important application of the present invention is in catheter delivery systems for self-expanding stents of nickel-titanium shape memory alloy, as well as for stent grafts and other covered stents based on such alloys. With such delivery systems, it is conventional to provide a pusher that abuts the stent and is effective to resist proximal movement of the stent during the period that the sheath surrounding the stent is being withdrawn proximally. In consequence, the shaft of the catheter of the delivery system exhibits a push element and a pull element. The pull element running along the shaft is functional to pull the radially confining sheath proximally to release the stent. The push element is capable of enduring a compressive stress along its length, that provides to the pusher that is abutting the stent the necessary pushing force to restrain the stent from moving proximally with the retreating sheath. The state of the art in such delivery systems is replete with examples of systems that use a wire as the pull element and a tubular member such as a stainless steel hypo tube as the pushing element that delivers the pushing force to the pusher that is abutting the stent. In such arrangements, a connection is needed, between the pull wire that runs the length of the catheter shaft, and the elongate pull element of the present invention, that pulls the sheath proximally to release the stent. It may be convenient to provide this connection in the form of a complete or partial ring to which the pull wire is brazed or welded, or otherwise fixed, thereby to extend proximally from the ring, while the elongate pull element a band of PET sheath material in preferred embodiments of the present invention) is bonded in some other way to the connector ring. For example, the connector ring could be provided as two components that snap-fit together, captivating the pull element between the two ring components when they snap together.

Stenting delivery systems are usually provided with rings that serve as radiopaque markers, so that the progress of the delivery system, and the progress of progressive stent release into the bodily lumen, can be monitored radioscopically. It is envisaged that the connector ring that connects the elongate pull element to a pull wire running the length of the shaft of the catheter is an element that lends itself to formulation as a radiopaque marker element. In that case, one envisages the connector ring being located close to the proximal end of the stent during the delivery phase, and moving proximally away from the stent pusher during deployment of the stent. Supposing that the stent pusher is itself serving as a radiopaque marker, the growing gap between the stent pusher and the connector ring, as seen radioscopically, serves as an indication of progress of stent release into the bodily lumen.

It will be apparent, then, to readers skilled in this art that the architecture of the distal end of the stent delivery system offers possibilities to get the passing diameter of that distal end zone down to values hitherto not obtained, because the sheath can be made of ultra-thin material.

Furthermore, it is possible to contemplate deployment of extremely long stents, simply because the sheath is being steadily withdrawn proximally from its location between the expanding stent and the tissue of the bodily lumen, all the while that the sheath is being progressively torn along the line of weakness from its distal end to its proximal end 1 leaving sandwiched between the stent and the bodily lumen, when stent deployment is complete, a much smaller amount of sheath material than would be the case with for example a sheath slitting "cheesewire" as in EP-A-732087 or WO 2001/008599 that slit the sheath but do not withdraw it proximally during the stent deployment period.

Other variations will be evident to those skilled in the art. Specifically, the idea of providing a pull element between two parallel lines of weakness, so that the arc of sheath material between the two lines of weakness is pulled proximally by the pull element, but not the arc on the other side of the diameter of the sheath, is an intermediate embodiment between the previously proposed "cheesewire" system in which the full circumference of the sheath continues to lie between the expanded stent and the wall of the bodily lumen, and the "single line of weakness" embodiment shown in the present drawings, in which the full circumference of the sheath is pulled proximally with the pull element 240. Suppose, for example, that the pull element 240 is a band that extends around a substantial part of the circumference of the sheath, for example, halfway around the circumference of the sheath. In such a case, proximal withdrawal of half the sheath material will leave for withdrawal after stent deployment sheath material amounting to only half of the circumference, instead of the prior art full circumference. This is worthwhile progress, especially with lengthy devices to be placed in the lumen.

Although the presently preferred material for the sheath is PET, this does not exclude other materials. Materials selection is part of the routine duties of the person skilled in the art when seeking to optimise stent delivery systems. For the present inventors, as of now, the "best mode" of realising the present invention involves using a sheath of PET, cold drawn (that is to say, drawn at a temperature of 50° C. or less) and with a wall thickness after cold drawing (and with the stent or stent graft inside the PET tube lumen) of 0.035 mm (or even less). Those skilled in the art will build on their specialist background knowledge when considering the above disclosures, factoring into their consideration of the present disclosure the specialist knowledge that they have from their own experience in this field. Quite evidently, engineers from other corporations will have their own design history and preferred ways of implementing the teachings set out above.

Readers will understand that the illustrated embodiments are non-limiting. Readers have enough background technical knowledge to modify the specific teachings above so as to conform to their own perceptions of good design and conformity with their own stent products or other requirements of the market.

The invention claimed is:

1. A method of loading a self-expanding stent into a delivery sheath that is by itself strong enough to preserve the stent in a radially compressed pre-deployment configuration designed for insertion into a vasculature, wherein in the radially compressed pre-deployment configuration, the stent is held compressed solely by the delivery sheath, comprising the steps of:
   providing a stent having a first end and a second end;
   compressing the stent to a diameter, d2;
   providing a loading sheath with an inner diameter d1;
   with the stent exhibiting an outside diameter of d2, where d2<d1, advancing the stent axially into the loading sheath into a first configuration wherein the loading sheath further comprises a stent region and the stent region accommodates the entire stent;
   advancing the loading sheath, containing the stent, into a lumen of the delivery sheath into a second configuration wherein the stent region is completely inside the delivery sheath; and
   deploying the stent into the lumen of the delivery sheath into a third configuration, by withdrawing the loading sheath while restraining the stent from axial movement out of the lumen of the delivery sheath.

2. Method according to claim 1, further comprising the step of, with the stent and delivery sheath in the third configuration, imposing lengthwise strain on the delivery sheath, to draw down the inner diameter of the delivery sheath to a diameter d3 which is less than d1.

3. Method according to claim 2, wherein the delivery sheath prior to said strain has a wall thickness of the order of 30 μm.

4. Method according to claim 2, wherein the delivery sheath exhibits a strain initiation zone from which the strain spreads out, progressively along the length of the delivery sheath.

5. Method according to claim 4, including the step of positioning the strain initiation zone between the first end and the second end of the stent.

6. Method according to claim 5, wherein the strain initiation zone is located mid-way between the first end and the second end of the stent.

7. Method according to claim 4, wherein the strain initiation zone comprises a portion of the delivery sheath that exhibits a reduced wall thickness.

8. Method according to claim 2, in which a tool is used to advance the stent into the delivery sheath, which tool has a portion that extends along at least a part of the length of a lumen of the stent.

9. Method according to claim 8, in which said tool is removed from the stent, before the step of drawing down the delivery sheath is completed.

10. Method according to claim 2, including a step of introducing into a lumen of the stent, before the step of drawing down the delivery sheath is completed, a component of a catheter delivery system for said stent.

11. Method according to claim 2, including a step of providing within the lumen of the delivery sheath, prior to drawing down said delivery sheath onto the stent, a splitter that lies between the stent and the drawn down delivery sheath, which splitter is capable when actuated, of splitting the delivery sheath to permit the stent to deploy.

12. Method according to claim 2, wherein a tool is used to impose the strain on the delivery sheath, the tool comprising first and second sheath grippers, one to grip each opposite end of the delivery sheath, beyond the respective end of the stent inside the delivery sheath.

13. Method according to claim 12, wherein at least one of the sheath grippers grips the delivery sheath all around the circumference of the delivery sheath.

14. Method according to claim 13, in which at least one of the grippers exhibits a high friction grip surface to contact the delivery sheath, which grip surface is of a silicone, rubber material.

15. Method according to claim 2, in which the sheath drawn down over the stent exhibits an outside diameter of not more than 6 French (2 mm).

16. Method according to claim 1, in which the delivery sheath is one which can be parted along a line extending axially the full length of the stent, to allow the stent to push the material of the longitudinally parted delivery sheath out of the way, during radial expansion of the stent that occurs as the stent deploys into a bodily lumen.

17. Method according to claim 1, wherein the delivery sheath is of polyethyleneterephthalate.

18. Method according to claim 1, wherein advancing the stent axially into the loading sheath is done while the loading sheath is held stationary.

19. Method according to claim 1, wherein when the stent and loading sheath are in the first configuration, the stent is in a compressed loading configuration, and wherein in the compressed loading configuration, the stent is held compressed solely by the loading sheath.

20. Method according to claim 1, wherein advancing the stent axially into the loading sheath includes advancing the stent into the loading sheath such that the stent is entirely contained within the loading sheath.

* * * * *